(12) United States Patent
Lisogurski et al.

(10) Patent No.: US 10,722,117 B2
(45) Date of Patent: Jul. 28, 2020

(54) SYSTEMS AND METHODS FOR STORING DATA ON MEDICAL SENSORS

(71) Applicant: COVIDIEN LP, Mansfield, MA (US)

(72) Inventors: Daniel Lisogurski, Boulder, CO (US); Rakesh Sethi, Vancouver (CA)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/222,807

(22) Filed: Dec. 17, 2018

(65) Prior Publication Data
US 2019/0223720 A1 Jul. 25, 2019

Related U.S. Application Data

(60) Provisional application No. 62/620,303, filed on Jan. 22, 2018.

(51) Int. Cl.
G08B 21/00 (2006.01)
A61B 5/00 (2006.01)
H04Q 9/00 (2006.01)
A61B 5/1455 (2006.01)

(52) U.S. Cl.
CPC ............ *A61B 5/0002* (2013.01); *A61B 5/746* (2013.01); *A61B 5/7425* (2013.01); *H04Q 9/00* (2013.01); *A61B 5/14552* (2013.01); *A61B 2560/0475* (2013.01)

(58) Field of Classification Search
CPC .......... A61B 2560/0475; A61B 5/0002; A61B 5/14552; A61B 5/7425; A61B 5/746; H04Q 9/00
USPC ....................................................... 340/870.07
See application file for complete search history.

(56) References Cited

U.S. PATENT DOCUMENTS

| | | | |
|---|---|---|---|
| 6,553,241 B2 | 4/2003 | Mannheimer et al. | |
| 6,801,797 B2 | 10/2004 | Mannheimer et al. | |
| 2002/0120187 A1* | 8/2002 | Eiffert | A61B 5/0002 600/407 |
| 2004/0006261 A1* | 1/2004 | Swedlow | A61B 5/14551 600/323 |
| 2004/0153344 A1* | 8/2004 | Bui | G06F 19/3418 705/3 |
| 2006/0229510 A1* | 10/2006 | Fein | A61B 5/14552 600/323 |
| 2010/0042862 A1* | 2/2010 | Sun | G06F 1/3215 713/340 |
| 2011/0082377 A1* | 4/2011 | Mahajan | A61B 5/0002 600/508 |
| 2011/0213216 A1* | 9/2011 | McKenna | A61B 5/0002 600/301 |
| 2012/0185267 A1* | 7/2012 | Kamen | G06Q 50/22 705/2 |
| 2018/0315285 A1* | 11/2018 | Janssen | A61B 5/746 |

\* cited by examiner

*Primary Examiner* — Mark S Rushing
(74) *Attorney, Agent, or Firm* — Cantor Colburn LLP (57) ABSTRACT

A system includes a monitor configured to be coupled to multiple sensors over time to monitor one or more physiological characteristics of one or more patients. A first sensor of the multiple sensors includes a sensor memory, and the monitor is configured to transfer information to the first sensor for storage in the sensor memory of the first sensor. The information includes information related to one or more sensors of the multiple sensors that were coupled to the monitor prior to the first sensor.

20 Claims, 4 Drawing Sheets

SYSTEMS AND METHODS FOR STORING DATA ON MEDICAL SENSORS

CROSS-REFERENCE TO RELATED APPLICATION

The present application claims priority to and the benefit of U.S. Provisional Application No. 62/620,303, entitled "SYSTEMS AND METHODS FOR STORING DATA ON MEDICAL SENSORS," filed on Jan. 22, 2018, the specification of which is hereby incorporated by reference in its entirety for all purposes.

BACKGROUND

The present disclosure relates generally to systems and methods for storing data on sensors, and, more particularly, to systems and methods for transferring data from a monitor to a sensor to facilitate various actions, such as sensor remanufacturing, sensor design, and/or analysis of sensor use in clinical settings.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring certain physiological characteristics of a patient. Such devices provide doctors and other healthcare personnel with the information they need to provide the best possible healthcare for their patients. As a result, such monitoring devices have become an indispensable part of modern medicine. For example, photoplethysmography is a common technique for monitoring physiological characteristics of a patient, and one device based upon photoplethysmography techniques is commonly referred to as pulse oximetry. Pulse oximeters may be used to measure and monitor various blood flow characteristics of a patient, such as the blood oxygen saturation of hemoglobin in arterial blood, the volume of individualized blood pulsations supplying the tissue, and/or the rate of blood pulsations corresponding to each heartbeat of a patient.

Pulse oximeters, and other medical devices, may utilize sensors to collect physiological data that may be provided to a monitor, which processes the data to calculate one or more physiological characteristics of a patient. However, such sensors are often discarded after use and/or information related to operation of the sensors is not provided to the manufacturer of the sensors.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical monitoring systems may include sensors and monitors. In operation, a sensor may be coupled to a monitor to enable patient monitoring. For example, upon coupling the sensor to the monitor, the monitor may receive information related to the sensor, such as a serial number of the sensor, a manufacturer of the sensor, an indicator of calibration coefficients and/or algorithms that should be used by the monitor to calculate one or more physiological characteristics, a number of prior uses of the sensor, and/or a number of prior remanufacturing events for the sensor. Additionally, the sensor may collect physiological data and provide the physiological data to the monitor, which processes the physiological data to calculate the one or more physiological characteristics of a patient. During patient monitoring, the monitor may determine, track, and/or record (e.g., in a memory of the monitor or database communicatively coupled to the monitor) other information related to the sensor, such as a duration of operation of the sensor, a compatibility between the sensor and the monitor (e.g., whether the sensor and the monitor are produced by the same manufacturer), a number and/or type of alarms generated during operation of the sensor, a level of ambient light present during operation of the sensor, and/or the one or more physiological characteristics of the patient obtained during operation of the sensor.

In some clinical settings, the sensor may be discarded following the patient monitoring session or at the end of the sensor's life. In some clinical settings, the sensor may be returned to the manufacturer for remanufacturing (e.g., reprocessing) to enable reuse of the sensor and/or separation of certain parts of the sensor (e.g., the emitter, the detector) for use in another sensor. However, when returned to the manufacturer, the sensor may not include any information related to operation of the sensor in the clinical setting. Thus, the manufacturer may not be aware of events that occurred during operation of the sensor or other information related to use of the sensor or the monitor in the clinical setting.

Advantageously, the present embodiments provide systems and methods that transfer various types of information related to the sensor, the monitor, and/or one or more sensors previously coupled to the monitor to a memory of the sensor. Thereafter, the information on the memory of the sensor may be retrieved and processed by a sensor processing system to facilitate various actions, such as sensor remanufacturing, sensor design, and/or analysis of sensor use in clinical settings, for example.

Although the embodiments described herein generally relate to pulse oximetry monitoring systems to facilitate discussion, it should be appreciated that the disclosed embodiments may be adapted or configured for any of a variety of monitoring systems that employ any of a variety of monitors and sensors. For example, the systems and methods described herein may, additionally or alternatively, include or be adapted for patient temperature monitoring systems, blood pressure monitoring systems, respiration monitoring systems, electrocardiogram monitoring systems, capnography systems, cerebral oximetry systems, among others.

Figure 1:
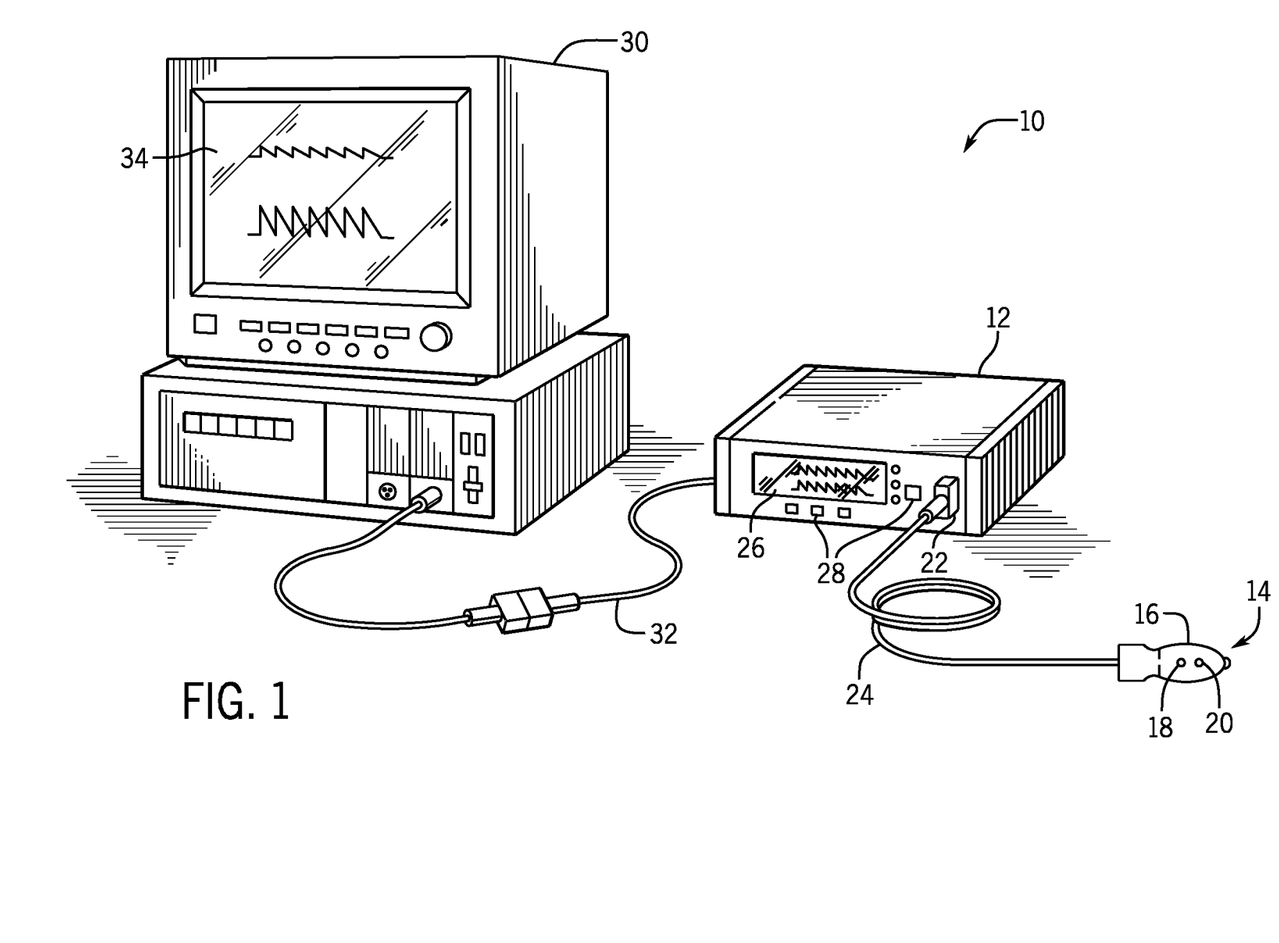
FIG. 1 is a perspective view of a monitoring system, in accordance with an embodiment of the present disclosure.

With the foregoing in mind, FIG. 1 depicts an embodiment of a medical monitoring system 10 having a monitor 12 (e.g., medical monitor) that may be used with multiple sensors 14 (e.g., medical sensors). The illustrated sensor 14 includes a sensor body 16 (e.g., housing) that supports one or more light sources 18 (e.g., emitters) configured to emit light into a tissue of a patient and one or more detectors 20 configured to detect light from the one or more light sources 18 after the light passes through the tissue of the patient. The one or more detectors 20 may be configured to generate a signal, such as a photoplethysmography signal, based on the detected light. The one or more detectors 20 may transmit and/or provide the signal to the monitor 12, which processes the signal to determine one or more physiological characteristics of the patient. In the illustrated embodiment, the sensor 14 is coupled to a sensor interface 22 (e.g., receptacle) of the monitor 12 via a cable 24.

As discussed in more detail below, in some embodiments, the monitor 12 may transfer information related to one or more other sensors that were previously coupled to the monitor 12 to the sensor 14 (e.g., to the memory of the sensor 14) while the sensor 14 is coupled to the monitor 12. In this manner, information related to multiple sensors 14 that were coupled to the monitor 12 and used in the clinical setting may be collected and stored on the sensor 14. It should be appreciated that, in some embodiments, information related to the sensor 14 itself, information related to the monitor 12, and/or information related to other devices or computing systems (e.g., other monitors, other sensors used with the other monitors, servers, databases) that are communicatively coupled to the monitor 12 may be transferred from the monitor 12 to the sensor 14. For example, a serial number of the monitor 12, a duration of operation of the monitor 12, faults or errors in operation of the monitor 12, software on the monitor 12, and/or setting changes input at the monitor 12 may be transferred from the monitor 12 to the sensor 14. Information related to the monitor 12 may correspond to a time that the monitor 12 is used with the sensor 12, or the information may correspond to a time prior to the time that the monitor 12 is used with the sensor 12 (e.g., a time during which one or more other sensors were coupled to the monitor 12). When the sensor 14 is returned to the manufacturer (or provided to another entity for processing), the manufacturer may retrieve the information and utilize the information to facilitate various actions, such as remanufacturing of the sensors, design of new sensors, and/or analysis of use of the sensors in clinical settings, for example. It should be appreciated that the information may also facilitate analysis of use of the monitor 12 in clinical settings.

In the illustrated embodiment, the monitor 12 includes a monitor display 26, which may be configured to display information regarding the one or more physiological characteristics, information about the sensor 14, and/or alarm indications, for example. The monitor 12 may also include various input components 28, such as knobs, switches, keys and keypads, buttons, etc., to facilitate operation and configuration of the monitor 12 and monitoring system 10 by a user.

In some embodiments, the monitor 12 may be coupled to other devices or computing systems, such as a multi-parameter monitor 30. In the illustrated embodiment, the monitor 12 is coupled to the multi-parameter monitor 30 via a cable 32. In addition to the monitor 12, or alternatively, the multi-parameter monitor 30 may be configured to calculate physiological parameters and to provide a central display 34 for visualization of information from the monitor 12 and from other medical devices, monitors, and/or monitoring systems. The multi-parameter monitor 30 may facilitate presentation of patient data, such as pulse oximetry data determined by the monitoring system 10 and/or physiological parameters determined by other patient monitoring systems (e.g., regional oxygen saturation monitor systems, bispectral index or electrocardiographic (ECG) monitoring system, a respiration monitoring system, a blood pressure monitoring system, etc.). For example, the multi-parameter monitor 30 may display a graph of $SpO_2$ values, a current pulse rate, a graph of blood pressure readings, an electrocardiograph, and/or other related patient data in a centralized location for quick reference by a medical professional. In some embodiments, the monitor 12 may be configured to access and transfer information related to the multi-parameter monitor 30 and/or information related to the other sensors and the other monitors used to obtain the other physiological parameters to the sensor 14.

Although the cables 22, 32 are illustrated, it should be understood that some or all of the components of the monitoring system 10 may be configured to communicate wirelessly via a network. For example, the monitor 12 may include a wireless transceiver that enables wireless communication with respective wireless transceivers of the sensor 14, the multi-parameter monitor 30, and/or other devices or computing systems.

Figure 2:
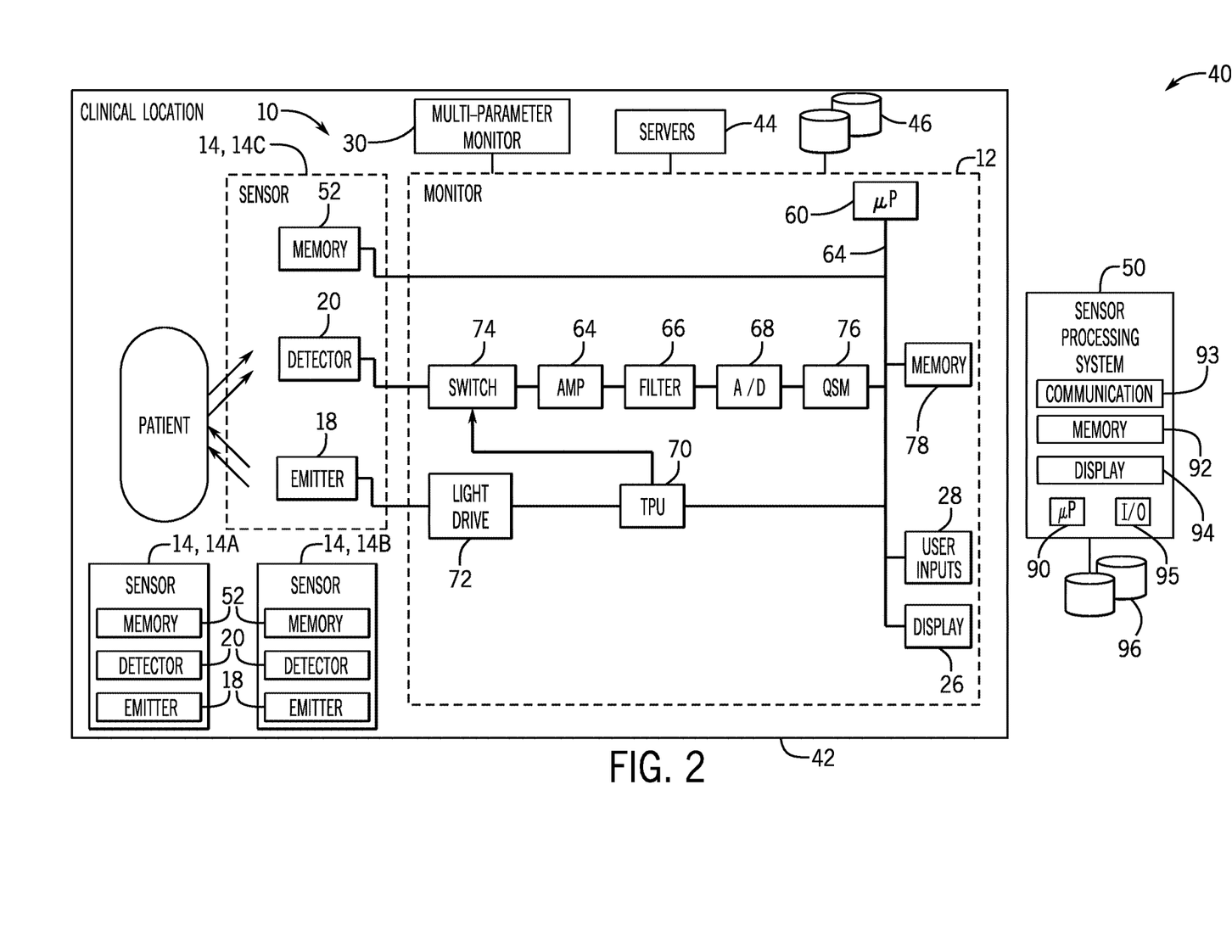
FIG. 2 is a block diagram of an information collection system that includes the monitoring system of FIG. 1 and a sensor processing system, in accordance with an embodiment of the present disclosure.

FIG. 2 is a block diagram of an information collection system 40. As shown, the information collection system 40 includes the monitoring system 10 and various other components that may be utilized at a clinical location 42 (e.g., doctor's office, hospital, or department within a hospital). For example, the information collection system 40 may include the monitoring system 10 having the monitor 12 that is used with multiple sensors 14 over time (e.g., sequentially over time). To facilitate discussion, a first medical sensor 14A (e.g., previous sensor), a second medical sensor 14B (e.g., previous sensor), and a third medical sensor 14C (e.g., current sensor) are shown in FIG. 2; however, it should be appreciated that the monitor 12 may be used with many more sensors 14 (e.g., tens, hundreds, or more) over time. Each sensor 14 includes one or more light sources 16, one or more detectors 18, and a memory 52. The memory 52 may be a random access memory (RAM), a read only memory (ROM), or any suitable type of programmable and/or erasable memory, for example.

Various other devices or computing systems may be utilized at the clinical location 42, such the multi-parameter monitor 30, one or more other computing systems or servers 44, one or more databases 46, or the like. As discussed in more detail below, the information collection system 40 may include a sensor processing system 50 that may be utilized by a manufacturer (or other entity) to retrieve and process information stored on the one or more sensors 14.

As shown, the monitor 12 may include various components to facilitate the techniques disclosed herein. In the illustrated embodiment, the monitor 12 includes a processor 60 coupled to an internal bus 62. The received signal from the one or more detectors 20 of the sensor 14 may be passed through an amplifier 64, a low pass or bandpass filter 66, and an analog-to-digital converter 68. A time processing unit (TPU) 70 may provide timing control signals to light drive circuitry 72, which controls when the one or more light sources 16 of the sensor 14 are activated, and, if multiple light sources are used, the multiplexed timing for the different light sources. The TPU 70 may also control the gating-in of signals from the sensor 14 through a switching circuit 74. These signals are sampled at the proper time, depending at least in part upon which of multiple light sources 18 is activated, if multiple light sources 18 are used. The digital data may then be stored in a queued serial module (QSM) 76, for later downloading to a memory 78 as the QSM 76 fills up. The monitor 12 may include the display 26 and the input components 28, such as knobs, switches, keys and keypads, touchscreens, buttons, etc., to provide for operation and configuration of the monitor 12.

The processor 60 may be any type of computer processor or microprocessor capable of executing computer-executable code. The memory 78 may be any suitable article of manufacture that can serve as media to store processor-executable code, information, or the like. These articles of manufacture may represent non-transitory computer-readable media (e.g., any suitable form of memory or storage) that may store the processor-executable code used by the processor 60 to perform the presently disclosed techniques. It should be noted that non-transitory merely indicates that the media is tangible and not a signal.

While the sensor 14 is coupled to the monitor 12, the monitor 12 may receive from the sensor 14 information related to the sensor 14, such as a serial number of the sensor 14, a manufacturer of the sensor 14, an indication of calibration coefficients and/or algorithms that should be used by the monitor 12 to calculate one or more physiological characteristics, a number of prior uses of the sensor 14, and/or a number of prior remanufacturing events for the sensor 14. As discussed in more detail below, such information may be stored in the memory 52 of the sensor 14 prior to a patient monitoring session (e.g., at manufacturing or during a prior use of the sensor 14) and transferred to the monitor 12 at the beginning of the patient monitoring session (e.g., in response to coupling the sensor 14 to the monitor 12).

The sensor 14 may collect physiological data and provide the physiological data to the monitor 12, which processes the physiological data to calculate the one or more physiological characteristics of a patient. The monitor 12 may provide instructions and/or operational parameters to the sensor 14. For example, the monitor 12 may provide light drive signals via the light drive circuitry 72 to illuminate the one or more light sources 18 of the sensor 14 to facilitate patient monitoring.

During the patient monitoring session, the monitor 12 may determine, track, and/or record (e.g., in the memory 78 of the monitor 12) other information related to the sensor 14, such as a duration of operation of the sensor 14, a compatibility between the sensor 14 and the monitor 12 (e.g., whether the sensor 14 and the monitor 12 are produced by the same manufacturer), a number and/or type of alarms generated during operation of the sensor 14, a level of ambient light present during operation of the sensor 14 (e.g., as detected by the one or more detectors 20), and/or the one or more physiological characteristics of the patient obtained during operation of the sensor 14. The other information related to the sensor 14 that is determined, tracked, and/or recorded during operation of the sensor 14 may be transferred from the monitor 12 to the sensor 14 itself at the end of the patient monitoring session (e.g., to the memory 52 of the sensor 14) and/or prior to decoupling the sensor 14 from the monitor 12. Additionally or alternatively, the information related to the sensor 14 that is transferred to the monitor 12 and/or the other information related to the sensor 14 that is determined, tracked, and/or recorded during operation of the sensor 14 may be stored for later transfer from the monitor 12 to one or more other sensors 14 that are subsequently coupled to the monitor 12.

As noted above, multiple sensors 14 may be utilized with the monitor 12 over time, and thus, the monitor 12 may obtain information (e.g., a duration of operation, a compatibility with the monitor 12, a number and/or type of alarms generated during operation, a level of ambient light present during operation, and/or the one or more physiological characteristics of the patient obtained during operation, a serial number, a manufacturer, a number of prior uses, and/or a number of prior remanufacturing events) related to each of the multiple sensors 14. Information related to one or more other sensors 14 that were previously coupled to the monitor 12 may be transferred from the monitor 12 to the sensor 14 while the sensor 14 is coupled to the monitor 12. The monitor 12 may transfer information, such as the information related to the one or more other sensors 14 at various times. In some embodiments, the monitor 12 may transfer the information in response to the sensor 14 being coupled to the monitor 12. In some embodiments, the monitor 12 may transfer the information prior to obtaining the physiological data from the patient using the sensor 14. In some embodiments, the monitor 12 may transfer the information while obtaining the physiological data from the patient using the sensor 14. In some embodiments, the monitor 12 may transfer the information and/or information related to the sensor 14 itself after the patient monitoring session ends. For example, upon receipt of an input via the input components 28 to stop the patient monitoring session, the monitor 12 may automatically transfer the information to the sensor 14.

In some embodiments, the monitor 12 may provide an indication (e.g., via the display 26 or other output device, such as a speaker) that the transfer is in progress and/or that the transfer is complete, which may notify a medical professional when to maintain the connection between the sensor 14 and the monitor 12 and/or when to disconnect the sensor 14 from the monitor 12, for example.

In some embodiments, the memory 52 of the sensor 14 may be erased after the information (e.g., some or all of the information stored on the memory 52 at manufacturing, such as the serial number of the sensor 14, the manufacturer of the sensor 14, the indication of calibration coefficients and/or algorithms, the number of prior uses of the sensor 14, and/or the number of prior remanufacturing events for the sensor 14, may be erased or deleted) is transferred from the memory 52 to the monitor 12, thereby increasing the amount of available storage space on the memory 52 to facilitate subsequent transfer of other information, such as the information related to the sensor 14 that is determined, tracked, and/or recorded during operation of the sensor 14 and/or information related to the one or more sensors 14 that were previously coupled to the monitor 12, from the monitor 12 to the memory 52 of the sensor 14. In some embodiments, the monitor 12 may receive an indication of an amount of available storage space in the memory 52 from the sensor 14 and/or determine the amount of available storage space in the memory 52 of the sensor 14, and the monitor 12 may identify and transfer an appropriate amount of information based on the amount of available storage space (e.g., to fill or substantially fill the available storage space).

In some embodiments, the sensor 14 may be configured to provide an output or instruction to the monitor 12 to request a particular type of information, and the monitor 12 may transfer the particular type of information in response to receipt of the output or instruction. For example, the manufacturer may wish to collect information related to a duration of operation for each of the sensors 14 coupled to the monitor 12. The manufacturer may then include instructions in the memory 52 of the sensor 14 that may be read by the processor 60 of the monitor 12 when the sensor 14 is coupled to the monitor 12 and that cause the processor 60 of the monitor 12 to transfer information related to the duration of operation of the sensor 14 coupled to the monitor 12 and/or the duration of operation for one or more sensors 14 previously coupled to the monitor 12. In some cases, the manufacturer may wish to collect information related to the monitor 12, and in such cases, the memory 52 of the sensor 14 may include instructions that cause the processor 60 of the monitor 12 to transfer a particular type of information related to the monitor 12.

In some embodiments, the manufacturer may include instructions on multiple sensors 14 to collect a large amount of one or more types of information or to collect certain types of information about certain types of sensors 14, for example. The instructions may request information related to a certain number of prior sensors 14, information related to a particular prior sensor 14 (e.g., having a unique serial number), and/or information related to one or more sensors 14 that were operated during a particular period of time (e.g., a particular day last month or the prior day). In some embodiments, the monitor 12 may receive an indication of an order of priority for various types of information from the sensor 14. In such cases, the monitor 12 may transfer the information to the sensor 14 in the order of priority until the available storage space in the memory 52 of the sensor 14 is filled or substantially filled. In this manner, the manufacturer may collect specific information of interest.

The monitor 12 may track and/or coordinate the transfer of the information to multiple sensors 14 so that the multiple sensors 14 together provide a complete set of the information obtained over time. For example, the monitor 12 may transfer a first subset or type of the information (e.g., a duration of operation for the sensors 14 or the information for a first set of sensors 14) to one sensor 14, a second subset or type of the information (e.g., a number of alarms for the sensors 14 or the information for a second set of sensors 14) to another sensor 14, and so on, until the complete set of available information (or the requested information), which may be related to sensors 14 that were coupled to the monitor 12 prior to the multiple sensors 14 and/or to the monitor 12, is transferred to the multiple sensors 14. In some embodiments, the monitor 12 may transfer overlapping or duplicate information to the sensors 14, which may facilitate successful transfer of the complete set of available information (or the requested information) to the manufacturer (e.g., even if some sensors 14 are lost or damaged).

To facilitate discussion, FIG. 2 illustrates the first sensor 14A and the second sensor 14B after being decoupled from the monitor 12 following consecutive patient monitoring sessions, and the third sensor 14C coupled to the monitor 12. Accordingly, the information related to the first sensor 14A, the second sensor 14B, and/or one or more other sensors 14 utilized prior to the first sensor 14A may be stored on the memory 78 of the monitor 12. Furthermore, the memory 52 of the first sensor 14A may contain information related to one or more sensors 14 that were coupled to the monitor 12 prior to the first sensor 14A. Additionally, the memory 52 of the second sensor 14B may contain information related to the first sensor 14A and/or the one or more sensors 14 that were coupled to the monitor 12 prior to the first sensor 14A. While the third sensor 14C is coupled to the monitor 12, the monitor 12 may transfer information related to the first sensor 14A, the second sensor 14B, and/or the one or more sensors 14 that were coupled to the monitor 12 prior to the first sensor 14A to the memory 52 of the third sensor 14C. It should be appreciated that each sensor 14A, 14B, 14C may additionally or alternatively include information related to itself and/or the monitor 12.

As noted above, each sensor 14A, 14B, 14C may include overlapping or duplicate information, or the information may be transferred in series so that each sensor 14A, 14B, 14C includes particular types or subsets of the information. The information may be provided to each sensor 14A, 14B, 14C according to instructions stored the respective memory 52 of each sensor 14A, 14B, 14C. For example, the first sensor 14A may include information related to a duration of operation of all sensors 14 that were coupled to the monitor 12 within a period of time (e.g., the last month, the last week, the last day), the second sensor 14B may include information related to a number of uses of all sensors 14 that were coupled to the monitor within the period of time, and the third sensor 14C may include information related to a number and/or a type of alarms during operation of all sensors 14 that were coupled to the monitor 12 within the period of time. By way of another example, the first sensor 14A may include information related to a duration of operation of a first subset of a certain number of sensors 14 (e.g., 5, 10, 15, 20, 25, or more) that were coupled to the monitor 12 prior to the first sensor 14A, the second sensor 14B may include information related to a duration of operation of a second subset of the certain number of sensors 14, and the third sensor 14C may include information related to a duration of operation of a third subset of the certain number of sensors 14, so that together, the sensors 14A, 14B, 14C provide a complete set of information related to the duration of operation of the certain number of sensors 14.

As noted above, in some cases, the sensors 14 may be returned to the manufacturer (or provided to another entity) for processing. Accordingly, the information collection system 40 includes the sensor processing system 50, which is configured to retrieve and/or process the information stored on the memory 52 of each sensor 14. In one embodiment, the sensor processing system 50 may include or may be coupled to one or more processors 90, one or more memory devices 92, one or more communication components 93, one or more displays 94, one or more input/output (I/O) ports 95, and/or one or more databases 96.

The processor 90 may be any type of computer processor or microprocessor capable of executing computer-executable code. The memory 92 may be any suitable article of manufacture that can serve as media to store processor-executable code, data, or the like. These articles of manufacture may represent non-transitory computer-readable media (e.g., any suitable form of memory or storage) that may store the processor-executable code used by the processor 90 to perform the presently disclosed techniques. It should be noted that non-transitory merely indicates that the media is tangible and not a signal.

The communication component 93 may be a wireless or wired communication component that may facilitate communication between the sensor processing system 50, the databases 96, and various other computing systems via a network, the Internet, or the like. The I/O ports 95 may be interfaces that may couple to the sensors 14 and/or other peripheral components, such as input devices (e.g., keyboard, mouse), other computing systems, and the like. The display 94 may be any suitable type of display screen that is configured to provide indications that may be visualized by a user. It should be noted that the components described above with regard to the sensor processing system 50 are examples and the sensor processing system 50 may include additional or fewer components relative to the illustrated embodiment In operation, the sensor processing system 50 may be configured to retrieve the information from each sensor 14 and store the information in the one or more databases 96. The information from each sensor 14 may be manually (e.g., by a user) or automatically (e.g., via the sensor processing system 50) matched to a clinical location (e.g., clinical location 42), such as by scanning a barcode returned with the sensors 14 or by using sales records that indicate that the monitor 12 used with the sensors 14 was previously sold to the clinical location. The information may be sorted and/or organized in the one or more databases 96 by the serial number of each sensor 14, by type of sensor (e.g., pediatric, adult, clip, wrap, disposable, reusable, etc.), by the monitor 12 used with the sensor 14, by the clinical location or site, or by various other categories. Thus, the information for a particular sensor 14, a particular type of sensor 14, and/or the information related to use of the sensors 14 and/or the monitor 12 at a particular clinical location may be efficiently accessed and analyzed to facilitate remanufacturing of the sensors 14, design of the sensors 14, and/or analysis of use of the sensors 14 in clinical settings, for example. Furthermore, in some cases, the serial number of each sensor 14 may be utilized by the sensor processing system 50 to identify and/or remove duplicate data for a particular sensor 14.

As noted above, in some embodiments, the information may be utilized to determine appropriate sensor remanufacturing or sensor design steps. For example, the sensor processing system 50 may process the information to determine and/or to provide an output (e.g., via the display 94) indicating that many sensors 14 of a certain type provided a high number of alarms and/or false alarms that were most likely due to the sensor 14 separating from a tissue of the patient (e.g., "sensor-off" alarms or sudden changes in light detected by the detector 20 led to the alarms). Accordingly, the sensors 14 of the certain type may be remanufactured or redesigned to include a stronger adhesive (e.g., for disposable wrap sensors), a stronger clip (e.g., for reusable clip sensors), or the like to improve contact with the tissue of the patient. By way of another example, the sensor processing system 50 may process the information to determine and/or to provide an output (e.g., via the display 94) indicating that many sensors 14 of a certain type are being used in areas with low ambient light (e.g., low-light clinical settings, such as neonatal intensive care units). Accordingly, the sensors 14 of the certain type may be remanufactured or redesigned to have less light-shielding components or more appropriate light-shielding components, thereby reducing the cost of the sensors 14, for example.

As noted above, the information may be utilized to determine characteristics related to the use of the sensors 14 and/or the monitor 12 in clinical settings. The sensor processing system 50 may process the information to determine and/or to provide an output (e.g., via the display 94) indicating that the sensors 14 of a certain type are being utilized on a particular type of patient (e.g., pediatric vs. adult), which in turn, may enable determination of whether the sensors 14 are being utilized for an appropriate type of patient in clinical settings. For example, neonates may have much higher heart rates than adult patients, and thus, the sensors 14 that were used with neonates will include an average or median heart rate that is over a predetermined threshold, such as greater than 80, 90, or 100 beats per minute. Furthermore, certain types of sensors 14 (e.g., small wrap sensors) may be designed for use with neonates. Accordingly the sensor processing system 50 may utilize information, such as serial numbers that indicate the type of sensors 14 and the physiological characteristics that indicate high heart rates, to determine and/or to provide the output indicating that the sensors 14 are being utilized appropriately or inappropriately (e.g., as intended by the manufacturer or according to the manufacturer's labeling).

In some embodiments, the sensor processing system 50 may process the information to determine and/or to provide an output (e.g., via the display 94) indicating that the sensors 14 and the monitor 12 are being utilized in a particular type of clinical setting (e.g., intensive care, emergency room, operating room, or other areas of care). In some cases, the pattern of use (e.g., duration, number of uses, levels of ambient light) of sensors 14 may vary across clinical settings. For example, intensive care units may have much longer duration of use and/or low levels of ambient light. Accordingly the sensor processing system 50 may utilize such information to determine and/or to provide the output indicating that the sensors 14 are being utilized in an intensive care unit. In some cases, the sensor processing system 50 may also utilize information related to the pattern of use in combination with other information, such as the serial numbers indicating the type of sensors 14, to determine and/or provide the output indicating that the sensors 14 are being utilized appropriately or inappropriately.

In some embodiments, the sensor processing system 50 may be configured to determine and/or to provide a recommendation (e.g., the output may be a recommendation). For example, the sensor processing system 50 may analyze the information, determine characteristics related to the use of the sensors 14 and/or the monitor 12 in clinical settings, provide the recommendation regarding remanufacturing or redesign of the sensors 14, and/or provide the recommendation regarding a communication (e.g., marketing, advice, instructions, notifications, alerts) for the clinical location. For example, the sensor processing system 50 may determine that a particular clinical location is utilizing the sensors 14 inappropriately or contrary to the manufacturer's recommendations (e.g., utilizing reusable clip sensors intended for use on adult patients on pediatric patients in an intensive care setting). In such cases, the sensor processing system 50 may generate an alert (e.g., a text message, an email message, or a printed notification), which may be provided to the manufacturer (e.g., on the display 94) and/or to the clinical location (e.g., via a network, such as the Internet). The sensor processing system 50 may similarly generate and provide various other recommendations (e.g., a recommendation to adjust light shielding, a recommendation to redesign an adhesive wrap, recommendation to update software on the monitor 12, recommendation to have the monitor 12 inspected or repaired) based on the information.

It should be appreciated that the determinations and/or the outputs may be based on information collected from many sensors 14 (e.g., tens, hundreds, or more), and that the determinations and/or the outputs may be specific to one or more particular clinical locations (e.g., based on analysis of all or some sensors 14 collected from the one or more particular clinical locations), to one or more particular monitors 12 (e.g., based on analysis of all or some sensors 14 that were connect to the one or more particular monitors 12), to one or more particular types of sensors 14 (e.g., based on analysis of all or some sensors 14 of the one or more particular types), or the like. Furthermore, while certain examples provided herein generally relate to the transfer of information related to sensors 14 to facilitate discussion, it should be appreciated that, additionally or alternatively, information related to the monitor 12 (e.g., a monitor serial number, a duration of operation of the monitor 12, faults or errors in operation of the monitor 12, software on the monitor 12, setting changes input at the monitor 12), the multi-parameter monitor 30, and/or other sensors or monitors communicatively coupled to the multi-parameter monitor 30 or to the monitor 12 may be transferred to the sensors 14 and utilized in the same manner. Additionally or alternatively, in some embodiments, the monitor 12 may access and transfer information from the servers 44 and/or one or more databases 46 to the sensor 14.

Figure 3:
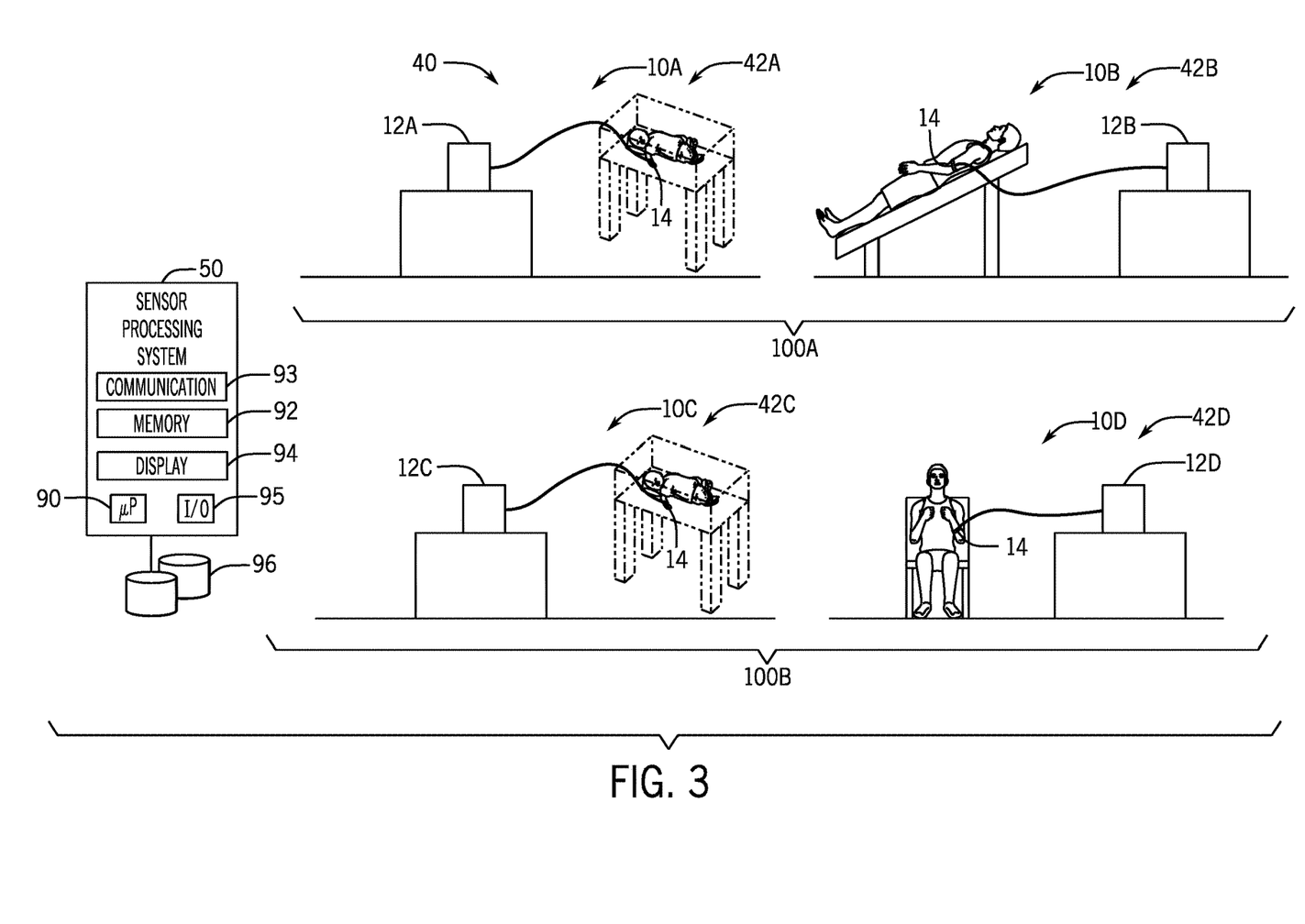
FIG. 3 is a schematic diagram of the information collection system of FIG. 2 illustrating that the sensor processing system may be used to process information from multiple monitoring systems, in accordance with an embodiment of the present disclosure.

FIG. 3 is a schematic illustration of the information collection system 40 with multiple monitoring systems 10 in multiple clinical locations 42. The information collection system 40 may be configured to collect information via multiple sensors 14 that are utilized in multiple monitoring systems 10 at multiple clinical locations 42. In the illustrated embodiment, a first monitor 12A is used in a first clinical location 42A of a first clinical site 100A (e.g., hospital), a second monitor 12B is used in a second clinical location 42B of the first clinical site 100A, a third monitor 12C is used in a third clinical location 42C of a second clinical site 100B (e.g., another hospital), and a fourth monitor 12D is used in a fourth clinical location 42D of the second clinical site 100B. Each of the monitors 12 may be used with multiple sensors 14 (e.g., tens, hundreds, or more sensors) over time, and the monitors 12 may transfer information to the multiple sensors 14 in the manner discussed above with respect to FIG. 2, for example. The multiple sensors 14 may then be returned or sent to the sensor processing system 50, which may process, store, and/or analyze the information in the manner discussed above with respect to FIG. 2, for example. Some examples are provided below to facilitate discussion; however, it should be appreciated that the information collected may be processed and analyzed make a variety of determinations and to facilitate a variety of actions.

With reference to FIG. 3, the information may be utilized to determine characteristics related to the use of each monitor 12 and/or the sensors 14 coupled thereto in the respective clinical locations 42. For example, the information may indicate that the first clinical location 42A is a neonatal intensive care unit (e.g., an average or median heart rate of the patients monitored with each sensor 14 is greater than a predetermined threshold, such as 80, 90, or 100 beats per minute; an average or median duration of use of each sensor 14 is greater than a predetermined threshold, such as 1, 2, or 3 days; an average or median detected ambient light level is less than a predetermined threshold; or any combination thereof). The information (e.g., the serial number) may also indicate that each sensor 14 that has been coupled to the first monitor 12A is a disposable wrap sensor intended for use in neonates. Accordingly, the sensor processing system 50 may determine and/or provide an output (e.g., via the display 94) indicating that the first clinical location 42A appears to be utilizing the appropriate type of sensor 14.

In some embodiments, the information may indicate that the ambient light levels are lower in the first clinical location 42A that the ambient light levels for which the sensors 14 being used there were designed. Accordingly, the sensor processing system 50 may determine and/or provide an output (e.g., via the display 94) indicating that at least the sensors 14 that will be provided to the first clinical location 42A may be redesigned with fewer or different light-shielding components, for example. Thus, in some embodiments, the information may facilitate a hospital-specific sensor design based on the information collected from each clinical location.

In some embodiments, the information may also indicate that the third clinical location 42C is a neonatal intensive care unit and that each sensor 14 that has been coupled to the third monitor 12C is a disposable wrap sensor intended for use in neonates. In some embodiments, the information may indicate that the ambient light levels are lower in both the first clinical location 42A and the third clinical location 42C than the ambient light levels for which the sensors 14 that are being used in these locations 42A, 42C were designed. Information from other neonatal intensive care units may provide the same indication. Accordingly, the sensor processing system 50 may determine and/or provide an output (e.g., via the display 94) indicating this type of sensor 14 (e.g., the entire line of disposable wrap sensors intended for neonates) may be redesigned with fewer or different light-shielding components, for example.

In some embodiments, the information received at the sensor processing system 50 may indicate that one or more sensors 14 were remanufactured by a third-party entity. For example, if the information indicates use of a particular sensor 14 (e.g., having a unique serial number) at the first clinical location 42A at the first clinical site 100A, and the information indicates later use of the same particular sensor 14 at the third clinical location 42C at the second clinical site 100B, but no record of remanufacturing (e.g., by the manufacturer) exists in the databases 94, then the sensor processing system 50 may determine that improper or unauthorized remanufacturing of the particular sensor 14 has likely occurred. In such cases, the sensor processing system 50 may generate an alert (e.g., a text message or an email message), which may be provided to the manufacturer (e.g., on the display 94) and/or to the third clinical site 42C (e.g., via a network, such as the Internet). In this manner, the manufacturer (or other entity) may track, collect information, and/or provide alerts regarding suspected remanufacturing events. Such information may also be utilized to determine which sensors 14 are eligible for remanufacturing and/or which sensors 14 should be discarded upon return to the manufacturer. For example, the sensor processing system 50 may analyze the information to determine and/or to provide an output indicating that certain sensors 14 were likely improperly remanufactured and/or should be discarded.

The information received at the sensor processing system 50 may be utilized in various other ways. For example, the information may indicate that the second clinical location 42B is an operating room (e.g., an average or median heart rate of the patients is less than a predetermined threshold, such as 60, 50, or 40 beats per minute; an average or median duration of use of each sensor 14 is within a predetermined range, such as 1-8, 2-5, or 3-4 hours; an average or median detected ambient light level is greater than a predetermined threshold; or any combination thereof). In some embodiments, the information may indicate that the ambient light levels are higher in the second clinical location 42A that the ambient light levels for which the sensors 14 that are being used there were designed. Accordingly, the sensor processing system 50 may determine and/or provide an output (e.g., via the display 94) indicating that at least the sensors 14 that will be provided to the third clinical location 42C should be redesigned with more light-shielding components, for example.

Similarly, the information may indicate that the fourth clinical location 42D is an emergency room (e.g., an average or median duration of use of each sensor 14 is less than a predetermined threshold, such as 1, 2, 3, or 4 hours; a number or prior uses exceeds a predetermined number of uses per day, such as more than 5, 6, 7, 8, 9, 10 or more uses per day; or any combination thereof). However, in some cases, the information may also indicate that one or more sensors that have been coupled to the fourth monitor 12D are incompatible with the four monitor 12D (e.g., manufactured by a third-party entity or different manufacturer). Accordingly, the sensor processing system 50 may determine that the fourth clinical location 42D has utilized incompatible sensors. In such cases, the sensor processing system 50 may generate an alert (e.g., a text message or an email message), which may be provided to the manufacturer (e.g., on the display 94) and/or to the fourth clinical site 42D (e.g., via a network, such as the Internet). In this manner, the information collection system 40 may collect information related to use of the sensors 14 and monitors 12 in clinical settings, and the information may be utilized to inform sensor remanufacturing, sensor design, and/or communications (e.g., marketing, advice, instructions, notifications, alerts) with each clinical site.

Figure 4:
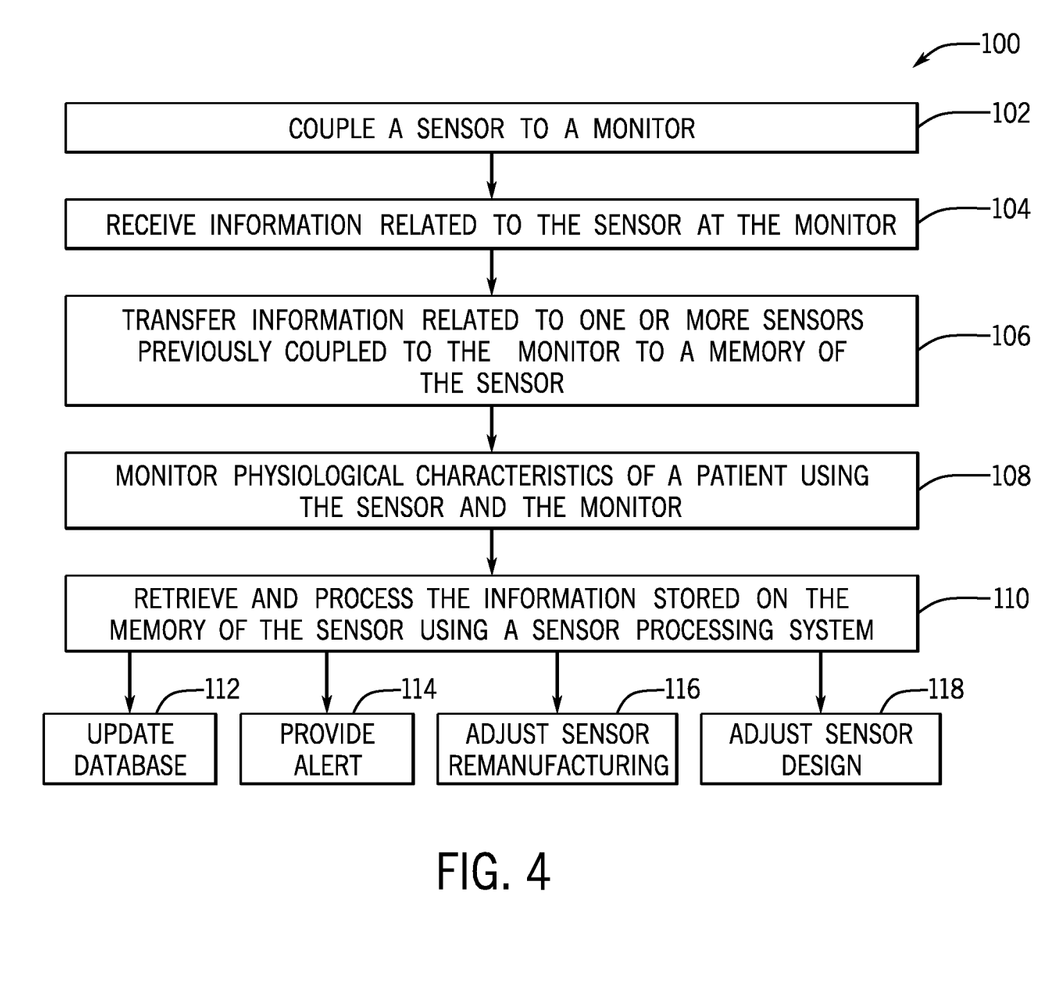
FIG. 4 is a flow diagram of a method of operating the information collection system of FIG. 2 to transfer information from a monitor to a sensor and to subsequently retrieve the information via the sensor processing system to facilitate various actions, in accordance with an embodiment of the present disclosure.

FIG. 4 is a process flow diagram of an embodiment of a method 100 of operating the information collection system 40. The method 100 includes various steps represented by blocks. Certain steps of the method 100 may be performed as an automated procedure by a system, such as the monitoring system 10 and/or the sensor processing system 50 that may be used within the information collection system 40. Although the flow chart illustrates the steps in a certain sequence, it should be understood that the steps may be performed in any suitable order, certain steps may be carried out simultaneously, and/or certain steps may be omitted, where appropriate. Further, certain steps or portions of the method 100 may be performed by separate devices. In addition, insofar as steps of the method 100 disclosed herein is applied to the received signals, it should be understood that the received signals may be raw signals or processed signals. That is, the method 100 may be applied to an output of the received signals.

In block 102, the sensor 14 may be coupled to the monitor 12 to facilitate patient monitoring. In block 104, while the sensor 14 is coupled to the monitor 12, the monitor 12 may receive from the sensor 14 information related to the sensor 14, such as a serial number of the sensor 14, a manufacturer of the sensor 14, an indication of calibration coefficients and/or algorithms that should be used by the monitor 12 to calculate the one or more physiological characteristics, a number of prior uses of the sensor 14, and/or a number of prior remanufacturing events for the sensor 14. Such information may be stored in the memory 52 of the sensor 14 at manufacturing and may be transferred to the monitor 12 at the beginning of a patient monitoring session (e.g., in response to coupling the sensor 14 to the monitor 12). As noted above, the memory 52 of the sensor 14 may be erased after (e.g., in response to) such information related to the sensor 14 is provided to the monitor 12. Such a configuration may increase an amount of available storage space on the memory of the sensor 14.

In block 106, information related to one or more other sensors previously coupled to the monitor 12 may be transferred from the monitor 12 to the sensor 14 while the sensor 14 is coupled to the monitor 12. The information may include a duration of operation of each sensor of the one or more other sensors, a compatibility between each sensor of the one or more sensors and the monitor 12 (e.g., whether the sensor and the monitor 12 are produced by the same manufacturer), a number and/or type of alarms generated during operation of each sensor of the one or more sensors, a level of ambient light present during operation of the each sensor of the one or more sensors (e.g., as detected by the one or more detectors 20), and/or the one or more physiological characteristics of the patient obtained during operation of each sensor of the one or more sensors, a serial number of each sensor of the one or more other sensors, a manufacturer of each sensor of the one or more other sensors, a number of prior uses of each sensor of the one or more other sensors, and/or a number of prior remanufacturing events for each sensor of the one or more other sensors.

The monitor 12 may transfer the information related to the one or more other sensors at various times while the sensor 14 is coupled to the monitor 12. In some embodiments, the monitor 12 may provide an indication (e.g., via the display 26 or other output device, such as a speaker) that the transfer is in progress and/or that the transfer is complete, which may notify a medical professional when to maintain the connection between the sensor 14 and the monitor 12 and/or when to disconnect the sensor 14 from the monitor 12, for example. In some embodiments, the sensor 14 may be configured to provide an output or instruction to the monitor 12 to request a particular type of information. In some embodiments, the monitor 12 may track and/or coordinate the transfer of the information to multiple sensors 14 over time.

As noted above, it should be appreciated that, additionally or alternatively, information related to the monitor 12 (e.g., a monitor serial number, a duration of operation of the monitor 12, software on the monitor 12, faults or errors in operation of the monitor 12, setting changes input at the monitor 12), the multi-parameter monitor 30, and/or other sensors or monitors communicatively coupled to the multi-parameter monitor 30 or to the monitor 12 may be transferred to the sensor 14. Furthermore, additionally or alternatively, the monitor 12 may access and transfer information from the server 44 and/or one or more databases 46 to the sensor 14.

In block 108, the sensor 14 may collect physiological data and provide the physiological data to the monitor 12, which processes the physiological data to calculate one or more physiological characteristics of a patient. The monitor 12 may provide instructions and/or operational parameters to the sensor 14. For example, the monitor 12 may provide light drive signals via the light drive circuitry 72 to illuminate the one or more light sources 18 of the sensor 14 to facilitate patient monitoring. During the patient monitoring session, the monitor 12 may determine, track, and/or record (e.g., in the memory 78 of the monitor 12) information related to the sensor 14, such as a duration of operation of the sensor 14, a compatibility between the sensor 14 and the monitor 12 (e.g., whether the sensor 14 and the monitor 12 are produced by the same manufacturer), a number and/or type of alarms generated during operation of the sensor 14, a level of ambient light present during operation of the sensor 14 (e.g., as detected by the one or more detectors 20), and/or the one or more physiological characteristics of the patient obtained during operation of the sensor 14. The other information related to the sensor 14 that is determined, tracked, and/or recorded during operation of the sensor 14 may be transferred from the monitor 12 to the sensor 14 at the end of the patient monitoring session (e.g., to the memory 52 of the sensor 14) and/or prior to decoupling the sensor 14 from the monitor 12. The information provided to the monitor 12 in block 104 and/or the other information related to the sensor 14 that is determined, tracked, and/or recorded during operation of the sensor 14 may additionally or alternatively be transferred from the monitor 12 to another sensor that is subsequently coupled to the monitor 12.

In block 110, the sensor processing system 50 may retrieve and/or process the information stored on the memory 52 of the sensor 14. As discussed above, multiple sensors 14 may be returned to the manufacturer (or other entity) to facilitate analysis of the information stored on the respective memories 52 of the multiple sensors 14, which in turn may provide a comprehensive picture of use of the sensors 14 and/or the monitors 12 in various clinical settings. The sensor processing system 50 may utilize the information to make various determinations and/or to provide various outputs (e.g., via the display 94).

For example, in step 112, the sensor processing system 50 may be configured to retrieve the information from each sensor 14 and store the information in the one or more databases 96. Additionally or alternatively, in step 114, the sensor processing system 50 may be configured to provide an alert or other communication based on the information. For example, in some such cases, the alert may be a text message indicating improper use of sensors 14, improper use of the monitor 12, use of incompatible sensors with the monitor 12, suspected unauthorized remanufacturing of sensors 14 by third-parties, or the like. The alert may be provided to the manufacturer (e.g., on the display 94) and/or to the clinical site (e.g., via a network, such as the Internet).

As noted above, the information may be used to facilitate sensor remanufacturing and/or sensor design. Accordingly, in step 116, the sensor processing system 50 may determine and/or provide an output (e.g., on the display 94) that may be used to inform the remanufacturing process. In some embodiments, the sensor processing system 50 may determine and/or provide a recommendation (e.g., do not remanufacture the sensor 14 or discard certain components of the sensor 14) for the sensor remanufacturing step. Similarly, in step 118, the sensor processing system 50 may determine and/or provide an output (e.g., on the display 94) that may be used to inform the sensor design process. In some embodiments, the sensor processing system 50 may determine and/or provide a recommendation (e.g., increase light-shield components for the sensors 14 of a certain type, provide stronger adhesive for the sensors 14 of a certain type, or the like) for the sensor design process. In this manner, the information collection system 40 may collect information related to use of the sensors 14 and monitors 12 in clinical settings, and the information may be utilized to during sensor remanufacturing, sensor design, and/or communications (e.g., marketing, advice, instructions, notifications, alerts) with each clinical site.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

What is claimed is:

1. A system, comprising:
a monitor configured to be coupled to multiple sensors over time to monitor one or more physiological characteristics of one or more patients; and
a first sensor of the multiple sensors, wherein the first sensor comprises a sensor memory, wherein the monitor is configured to transfer information to the first sensor for storage in the sensor memory of the first sensor, and the information comprises information related to one or more sensors of the multiple sensors that were coupled to the monitor prior to the first sensor.

2. The system of claim 1, wherein the information comprises a duration of operation of each sensor of the one or more sensors, an indication of compatibility between each sensor of the one or more sensors and the monitor, a number of alarms generated during operation of each sensor of the one or more sensors, a number of recorded reprocessing events for each sensor of the one or more sensors, a number of prior uses for each sensor of the one or more sensors, a level of ambient light present during operation of each sensor of the one or more sensors, or the one or more physiological characteristics of one or more patients obtained during operation of each sensor of the one or more sensors, or any combination thereof.

3. The system of claim 1, wherein the monitor is configured to automatically transfer the information to the first sensor in response to the first sensor being coupled to the monitor.

4. The system of claim 1, wherein the first sensor is configured to transfer first sensor information from the sensor memory to the monitor in response to the first sensor being coupled to the monitor, wherein the first sensor information comprises a serial number of the first sensor, calibration coefficients or information, a number of recorded reprocessing events for the first sensor, a number of prior uses of the first sensor, or a combination thereof.

5. The system of claim 4, wherein the first sensor is configured to erase the first sensor information from the sensor memory in response to transferring the first sensor information to the monitor.

6. The system of claim 5, wherein the monitor is configured to transfer the information to the sensor memory in response to the first sensor information being erased from the sensor memory.

7. The system of claim 1, comprising a sensor processing system configured to access the information in the sensor memory of the first sensor, wherein the sensor processing system comprises a processor configured to process the information to determine a clinical area of care in which the monitor was located during operation of the one or more sensors.

8. The system of claim 1, wherein the information comprises information related to the monitor.

9. The system of claim 1, wherein the monitor is configured to transfer first sensor information to the first sensor for storage in the sensor memory of the first sensor in response to an input indicating that the first sensor will be uncoupled from the monitor, and the first sensor information comprises a duration of operation of the first sensor, an indication of compatibility between the first sensor and the monitor, a number of alarms generated during operation of the first sensor, a level of ambient light present during operation of the first sensor, the one or more physiological characteristics of the one or more patients obtained during operation of the first sensor, or any combination thereof.

10. The system of claim 1, comprising a sensor processing system configured to access the information in the sensor memory of the first sensor, wherein the sensor processing system comprises a processor configured to process the information to generate an output that may be utilized to update a design of future sensors.

11. The system of claim 10, wherein the output comprises an indication of ambient light levels present during operation of the one or more sensors.

12. The system of claim 1, wherein the first sensor is configured to provide an instruction to the monitor while coupled to the monitor, and the instruction instructs the monitor to transfer a particular subset of the information to the first sensor.

13. The system of claim 1, wherein the monitor is configured to determine an amount of available space on the sensor memory of the first sensor and to transfer a subset of the information to the first sensor based at least in part on the amount of available space.

14. The system of claim 1, comprising a sensor processing system configured to access the information in the sensor memory of the first sensor, wherein the sensor processing system comprises a processor configured to process the information to generate an alert and a communication device that is configured to provide the alert to a clinical site.

15. A system, comprising:
a first sensor comprising a sensor memory storing information related to one or more other sensors that were coupled to a monitor prior to the first sensor; and
a sensor processing system configured to access the information in the sensor memory of the first sensor, wherein the sensor processing system comprises a processor configured to process the information to determine a clinical area of care in which the monitor was located during operation of the one or more other sensors and a display configured to provide an output indicating the clinical area of care.

16. A method, comprising:
monitoring one or more physiological characteristics of a patient using a first sensor coupled to a monitor; and
transferring information related to one or more sensors that were coupled to the monitor prior to the first sensor from the monitor to a sensor memory of the first sensor automatically in response to the first sensor being coupled to the monitor.

17. The method of claim 16, wherein the information comprises a duration of operation of each sensor of the one or more sensors, an indication of compatibility between each sensor of the one or more sensors and the monitor, a number of alarms generated during operation of each sensor of the one or more sensors, a number of recorded reprocessing events for each sensor of the one or more sensors, a number of prior uses for each sensor of the one or more sensors, a level of ambient light present during operation of each sensor of the one or more sensors, or the one or more physiological characteristics of one or more patients obtained during operation of each sensor of the one or more sensors, or any combination thereof.

18. The method of claim 16, comprising determining, using a processor of the monitor, an amount of available space on the sensor memory of the first sensor, wherein transferring the information comprises transferring a subset of the information to the first sensor based at least in part on the amount of available space.

19. The method of claim 16, comprising:
accessing, using a processor of a sensor processing system, the information from the sensor memory;
processing, using the processor, the information to determine a condition present during operation of the one or more sensors; and
providing, using the processor, a recommendation to update a design feature of future sensors based on the condition present during operation of the one or more sensors.

20. The method of claim 16, comprising determining, using a processor of a sensor processing system, a clinical area of care in which the monitor was located during operation of the one or more sensors based on the information.

* * * * *